United States Patent [19]
Breivik et al.

[11] Patent Number: 5,945,318
[45] Date of Patent: Aug. 31, 1999

[54] REFINING OIL COMPOSITIONS

[75] Inventors: Harald Breivik, Skjelsvik, Norway; Gudmundur G. Haraldsson, Reykjavik, Iceland

[73] Assignee: Norsk Hydro A.S., Oslo, Norway

[21] Appl. No.: 08/714,042

[22] PCT Filed: Mar. 7, 1995

[86] PCT No.: PCT/NO95/00050

§ 371 Date: Sep. 6, 1996

§ 102(e) Date: Sep. 6, 1996

[87] PCT Pub. No.: WO95/24459

PCT Pub. Date: Sep. 14, 1995

[30] Foreign Application Priority Data

Mar. 8, 1994 [GB] United Kingdom ............ 9404483

[51] Int. Cl.⁶ ............... C12P 7/62; C12P 7/64; C12N 9/20; C11C 1/00
[52] U.S. Cl. ............ 435/134; 435/135; 435/174; 435/176; 435/198; 435/271; 435/262; 514/560; 554/185; 554/186
[58] Field of Search ............ 435/134, 135, 435/198, 262, 174, 176, 271; 514/560; 554/185, 186

[56] References Cited

U.S. PATENT DOCUMENTS

| | | | |
|---|---|---|---|
| 4,377,525 | 3/1983 | Fujita et al. | 554/185 |
| 4,377,526 | 3/1983 | Fujita et al. | 260/424 |
| 4,792,418 | 12/1988 | Rubin et al. | 554/186 |
| 4,956,286 | 9/1990 | Macrae | 435/134 |
| 4,956,287 | 9/1990 | Suzuki et al. | 435/134 |
| 5,316,927 | 5/1994 | Zaks et al. | 435/134 |
| 5,480,787 | 1/1996 | Negishi et al. | 435/134 |
| 5,502,077 | 3/1996 | Breivik et al. | 514/560 |

FOREIGN PATENT DOCUMENTS

| | | |
|---|---|---|
| 59-14793 | 1/1984 | Japan. |
| 60-234588 | 11/1985 | Japan. |
| 62-091188 | 4/1987 | Japan. |
| 1-252294 | 10/1989 | Japan. |
| 2-25447 | 1/1990 | Japan. |
| 6-116585 | 4/1994 | Japan. |
| WO87/03899 | 7/1987 | WIPO. |
| WO 90/13656 | 11/1990 | WIPO. |
| WO90/13656 | 11/1990 | WIPO. |
| WO 90/16443 | 10/1991 | WIPO. |
| WO91/16443 | 10/1991 | WIPO. |

OTHER PUBLICATIONS

Li, Z., et al., "Lipase–Catalyzed Alcoholysis to Concentrate the N–3 Polyunsaturated Fatty Acid of Cod Liver Oil", *Enzyme Microb. Technol.*, 15(7):601–606 (1993).

Hoshino, T., et al., "Bioreactor for Enzymatic Reaction of Fat and Fatty Acid Derivatives. Part XII. Selective Hydrolysis of Fish Oil By Lipase to Concentrate N–3 Polyunsaturated Fatty Acids," *Agric. Voil. Chem.* 54(6):1459–1467 (1990).

Adachi, S., et al., "Acidolysis of Sardine Oil by Lipase to Concentrate Eicosapentaenoic and Docosahexaenoic Acids in Glycerides," *J. Ferment. Bioeng.* 75(4):259–264 (1993).

Zuyi et al., Enzyme Microb. Technol. 15(7), 601–6 (1993).

Zuyi et al., Biotechnol. Lett., 15(4), 393–8 (1993).

Lie, et al., "Digestive Lipolytic Enzymes in Cod (*Gadus Morrhua*): Fatty Acid Specificity", *Comp. Biochem. Physiol.*, vol. 80B, No. 3, pp. 447–450, 1985.

Lie, et al., "Fatty Acid Specificity of Candida cylindracea Lipase", *Fette, Seifen, Anstrichmittel*, vol. 88, No. 9, pp. 365–367, 1986.

English Abstract of Japanese Laid–Open Patent Application No. 59–14793, Jan. 1984.

Takagi, "Fractionation of Polyenoic Acids from Marine Lipids with Lipase", *Am. Oil Chem. Soc.*, vol. 66, pp. 488–489, 1989.

Haraldsson, et al. "Studies on the Positional Specificity of Lipase from *Mucor miehei* during Interesterification Reactions of Cod Liver Oil with n–3 Polyunsaturated Fatty Acid and Ethyl Ester Concentrates", *Acta Chemica Scandinavica*, vol. 45, pp. 723–730, 1991.

*Primary Examiner*—Leon B. Lankford, Jr.
*Assistant Examiner*—Christopher R. Tate
*Attorney, Agent, or Firm*—Fitzpatrick, Cella, Harper & Scinto

[57] ABSTRACT

This invention relates to a process for treating an oil composition containing saturated and unsaturated fatty acids in the form of triglycerides, with at least some of the unsaturated fatty acids being polyunsaturated, in order to obtain a refined product with a higher concentration of the polyunsaturated fatty acids.

29 Claims, 2 Drawing Sheets

REFINING OIL COMPOSITIONS

FIELD OF INVENTION

This invention relates to a novel process for treating an oil composition containing saturated and unsaturated fatty acids in the form of glycerides, in order to obtain a refined product with higher concentrations of the polyunsaturated fatty acids. The invention in particularly preferred embodiments provides a process for increasing the concentrations of EPA and DHA in a fish oil composition.

BACKGROUND OF THE INVENTION

In this specification polyunsaturated fatty acids are identified according to the system wherein the omega- or n-number denominates the position of the first double bond when counting from the terminal methyl group, e.g. in an omega-3 or n-3 fatty acid, the first double bond occurs at the third carbon carbon-bond from the terminal methyl group of the acid. Further, when a fatty acid is identified, for instance, as C18:3, this refers to a fatty acid having 18 carbon atoms in the chain and three double bonds.

Commercially important polyunsaturated fatty acids are EPA (eicosapentaenoic acid, C20:5) DHA (docosahexaenoic acid, C22:6) and AA (arachidonic acid, C20:4). The full nomenclature of these acids according to the IUPAC system is:

EPA
cis-5,8,11,14,17-eicosapentaenoic acid
DHA
cis-4,7,10,13,16,19-docosahexaenoic acid
AA
cis-5,8,11,14-eicosatetraenoic acid As is well known, EPA and DHA are proving increasingly valuable in the pharmaceutical and food supplement industries in particular. These acids are found in relatively high concentrations in certain marine oils, but for many purposes it is necessary that the marine oils should be refined in order to increase the content of EPA and/or DHA to suitable levels, or to reduce the concentrations of, or even eliminate, certain other substances which occur naturally in the raw oil. For pharmaceutical and food purposes, for instance, it is necessary to substantially completely eliminate all the pesticide residues which commonly occur in marine oils, even those derived from fish caught in sea areas quite remote from intensively cultivated land areas.

EPA and DHA must exhibit an all-cis (Z—Z) configuration corresponding to their naturally occurring state if they are to exhibit biological activity without toxicity. However, these acids are extremely fragile when they are heated and they very readily undergo fast oligomerization, isomerization and peroxidation reactions. Accordingly, it is extremely difficult to purify marine oil compositions containing EPA and DHA without risking loss of these desired acids in their useful form.

EPA and DHA occur in marine oils predominantly as their triglycerides. Up until now, most practical refining processes start either by esterifying the oil with a low molecular weight alcohol (normally ethanol) or by hydrolysing the oil to form free acids or their salts, whereafter fractionation of the oil to recover the desired product is initiated.

However, because of the complexity of marine raw materials, polyunsaturated fatty acid derivatives in highly purified form are not easily prepared by any single fractionation technique. Usually a combination of techniques is therefore used, the particular combination chosen depending on the composition of the raw material and the concentration and other quality criteria that are desired for the product. Urea complexation is one fractionation technique which is commonly employed in processes for recovering high content EPA and/or DRA compositions.

Urea has the useful property of forming solid complexes with straight-chain organic compounds. When a marine oil composition containing fatty acids or esters is added to a solution of urea, a crystalline complex is formed with the more saturated fraction of the acids. The crystals can be removed, leaving a raffinate of more unsaturated fatty acids or fatty acid esters.

Urea complexation has been used with both free fatty acids, and with methyl or ethyl esters of the fatty acids. The process can be made continuous by using heat exchangers with a scraped surface as reactors for urea occlusion formation. When fractionating esters, it seems to be the normal procedure first to react the oil with alcohol and/or alcohol/water and then to isolate the esters/free fatty acids before urea complexation. However, a combined in situ esterification and urea fractionation may also be performed as described in EP-A-0255824.

When such a process is used in combination with, for instance, two or more steps of molecular distillation, it is possible to produce a refined product containing 85% by weight or higher of n-3 polyunsaturated fatty acids, predominantly EPA and DHA from a raw marine oil. However, the total recovery of the refined product is undesirably low. In a typical commercial operation using such conventional fractionation processes, one might expect to recover only about 60–80 tons of an 85% n-3 fatty acid concentrate from 1000 tons of raw marine oil, i.e. a recovery rate of only 6–8%. This poor yield means not only that such refining processes are very expensive but also that they require bulky, complex equipment.

The lipophilic character of many environmental pollutants (examples: pesticides and polychlorinated biphenyls) results in an accumulation of these compounds in marine lipids. Unfortunately, urea does not form complexes with many such pollutants, and as a result a concentrate from urea complexation will contain increased, and for many purposes unacceptably high, levels of pesticides and other environmental pollution products as compared with the original marine oil. Consequently, current refining processes based on urea complexation for making refined fish oils for human consumption have to include complex and expensive purification procedures to reduce pollutant levels to acceptable values.

The present invention aims to provide an improved process for increasing the polyunsaturated fatty acid content of oil compositions, and particularly a process which is well adapted to a commercial process for recovering EPA and/or DHA from fish oil in enhanced yield.

As is known, lipases are well suited for use as catalysts in processes involving highly labile n-3 polyunsaturated fatty acids, such as EPA and DHA, occurring in marine oil. This is due to their ability to act at low temperatures, their neutral pH and their mildness in action, which helps keep to a minimum undesired side reactions such as cis-trans isomerizations, double-bond migrations, polymerizations, oxidations, etc. Thus, the utilization of lipases for the hydrolysis of fatty acids in marine oil is already well documented.

For instance, Lie and Lambertsen in Comp. Biochem. Physiol. 80B No. 3, pages 447–450, 1985, reported that intestinal lipase obtained from cod hydrolysed preferentially the polyunsaturated fatty acids 18:4, 20:5 and 22:6 present as triglycerides in capelin oil. They reported that this specificity was particularly prominent for the acid 20:5, i.e. EPA.

On the other hand, Lie and Lambertsen also found that the $C_{14}$–$C_{18}$ saturated and monounsaturated fatty acids were preferentially hydrolysed as triglycerides from capelin oil by *Candida cylinracea* lipase, whereas the long-chain monoenes, C20:1 and C22:1 and particularly the polyunsaturated fatty acids C18:4, and, to a lesser extent EPA, DHA were resistant to hydrolysis (Lie and Lambertsen, Fette, Seifen, Anstrichmittel, 88, 365, 1986).

A Japanese patent specification No. 59–14793—Noguchi et al, describes a method based on similar discrimination by lipases between saturated and unsaturated acids for is preparing concentrates of highly polyunsaturated fatty acids. Ethyl esters from miscellaneous marine oils such as sardine and mackerel oil were hydrolysed with various lipases (*Candida cylinracea, Aspergillus rhizopus* and *Mucor miehei*). Selective hydrolysis afforded ethyl ester concentrates of up to 25% EPA and 17% DHA after separation of the hydrolysed fatty acids.

Another Japanese patent, 172691—Nippon Oil and Fats, 1990 describes a method based on the hydrolysis of marine oil with Candida sp. lipase. EPA or its ester was obtained from a free fatty acid component and DHA or its ester from the residual glyceride component. The continuation of the process involved separation of fatty acid and glyceride components, esterification with lower alkyl, concentration of polyunsaturated fatty acids using urea complexion and further purification by molecular distillation, super-critical $CO_2$ fluid extraction or liquid chromatography. Takagi (Am. Oil Chem. Soc. 66, 488, 1988) has described a method based on the reverse process for separating EPA and DHA using an immobilized *Mucor miehei* lipase.

Polyunsaturated fatty acid concentrates obtained from Japanese sardine oil by the urea adduct method were esterified with methanol in n-hexane medium at room temperature. The lipase discriminated between EPA and DHA and selective esterification afforded an EPA enriched methyl ester concentrate of 5% EPA and 6% DHA as well as a DHA enriched free fatty acid concentrate of 52% DHA and 12% EPA in the ratio of 59 to 41, respectively.

Yamane and co-workers have very recently used several lipases to selectively hydrolyse cod liver oil and refined sardine oil (Agric. Biol. Chem. 54, 1459, 1990). The best results were obtained for the non-regiospecific *Candida cylindracea* and 1,3-specific *Aspergillus niger* lipases, but none of the lipases were able to raise the EPA content of the glyceride products significantly.

It is apparent from this prior work on the use of lipases to hydrolyse esters of marine oil fatty acids that different lipases behave quite differently, and also that a quite marked selectivity between one fatty acid and another, or between one type of fatty acid and another, is often exhibited by the lipases.

This substrate selectivity of certain lipases is taken advantage of by Zuyi and Ward who have described a lipase-catalysed alcoholysis of cod liver oil to prepare an n-3 polyunsaturated fatty acid-enriched fraction (Zuyi and Ward, "Lipase-catalyzed alcoholysis to concentrate the n-3 polyunsaturated fatty acid of cod liver oil", Enzyme Microb. Technol., 1993, 15, July, 601–606). The authors studied nine lipases and they found that Pseudomonas sp. lipase (CES from Amano International Enzyme Co) alcoholized fish oil at a higher rate than the other lipases and produced monoglycerides significantly enriched in EPA and DHA. In this prior process, the alcohol (ethanol and isopropanol were used) was employed both as a reactant and as a solvent for the reaction.

Zuyi and Ward studied the effect of water concentration in the reaction medium and they found that the alcoholysis (with isopropanol) by lipase CES increased with water content in the range 0–7.5% v/v. The data presented shows that a water content of 5% v/v was optimal, and that even with a water content of 2.5% v/v over 40% of the original triglycerides present in the oil remained unreacted after 12 hours (it is understood that these water contents refer to water added to the reaction system and take no account of the small amounts of water inevitably present in the fish oil and the "dry" enzyme). Concomitantly, there was very considerable hydrolysis of triglyceride to free fatty acid (typically more than 30%), for instance at a water content of 5% v/v there was 18.9% hydrolysis (compared with only 15.5% alcoholysis).

Although the Zuyi and Ward process is of scientific interest it does not, unfortunately, provide an improved process for preparing purified EPA/DHA compositions commercially. In particular, the inevitable presence in the lipase-catalysed product of significant quantities of free fatty acid make it difficult subsequently to purify the desired n-3 polyunsaturated fatty acids. For example, due to low volatility the free fatty acids cannot be separated from the glycerides by conventional molecular distillation techniques. Furthermore, since the esters and the free fatty acids have substantially different polarities, whilst the mono- and di-glycerides are of intermediate polarities, they cannot be separated from the glycerides using extraction. As demonstrated below, the present invention in contrast advantageously may use molecular distillation techniques not only to separate polyunsaturated fatty acid glycerides from saturated and monounsaturated fatty acid esters but also to simultaneously effect removal of environmental pollutants such as pesticides and polychlorinated biphenyls from the desired polyunsaturated fatty acid glyceride fraction.

SUMMARY OF INVENTION

We have now unexpectedly found, in accordance with the present invention, that certain specific lipases, including the Pseudomonas sp. lipase used by Zuyi and Ward, can be used to selectively transesterify the ester moieties of saturated and monounsaturated fatty acids in marine oil triglycerides under substantially anhydrous reaction conditions. It is found that such transesterification leads, without substantial concomitant hydrolysis, to a mixture of monoesters of the more susceptible saturated fatty acids, with the remaining n-3 polyunsaturated long-chain fatty acids being still bound to the glycerol moiety as esters, mainly mono- and diglycerides but also triglycerides, depending upon the extent of conversion.

More particularly, the present invention provides a process for treating an oil composition containing saturated and unsaturated fatty acids in the form of triglycerides, in order to obtain a refined product with higher concentrations of polyunsaturated fatty acids, which process comprises:

(a) subjecting the oil composition to a transesterification reaction with a $C_1$–$C_6$ alcohol under substantially anhydrous conditions and in the presence of a lipase active to preferentially catalyze the transesterification of the saturated and monounsaturated fatty acids, the amount of said $C_1$–$C_6$ alcohol present in the reaction being not more than 15 molar equivalents based on the triglycerides present; and thereafter (b) separating a residual fraction enriched in glycerides of polyunsaturated fatty acids from a fraction containing saturated and monounsaturated fatty acid esters produced by said lipase-catalyzed transesterification reaction.

As noted, the process of the present invention utilizes a lipase which is active to preferentially catalyse the transesterification of the saturated and monounsaturated fatty acids in the marine oil. We have found that many lipases either have relatively poor or indeed no activity in the transesterification reaction of this invention, or display a poor selectivity as between saturated and monounsaturated fatty acids on the one hand and polyunsaturated fatty acids, on the other hand. This is true, for instance, of *Geotrichum candidum* (GCL; Amano GC), *Aspergillus niger* (ANL; Amano A), *Candida rugosa* (CRL; Amano AY), *Chromobacterium viscosum* (CVL; Sigma), *Humicula lanuginosa* (HLL; Amano CE), *Rhizopus delemar* (RDL; Amano D), *Rhizopus oryzae* (ROL; Amano F), *Penicillium camembertii* (PCL; Amano G), *Candida lipolytica* (CLL; Amano L), *Mucor javanicus* (MJL; Amano M) and *Rhizopus niveus* (RNL; Amano N). *Candida antarctica* (CAL; Novo SP435) was found to be highly active in the transesterification reaction but unfortunately displayed little or no selectivity between the different classes of fatty acids and therefore is not suitable for use in the present invention.

Examples of lipases which we have found are operable in the process of the present invention include *Mucor miehei* lipase (MML; Novo Lipozyme), which displays good transesterification activity and reasonable selectivity as between polyunsaturated fatty acids and saturated and monounsaturated fatty acids; *Candida cylinracea* (CCL; Sigma) and *Penicillium roguefortii* (PRL; Amano R) lipases, both of which exhibit satisfactory selectivity although their activity is lower than some other lipases; and *Pseudomonas fluorescens* (PFL; Amano PS) and Pseudomonas sp. (PSL; Amano AK) lipases, both of which exhibit good activity and selectivity and therefore are often preferred for use in the invention.

Immobilisation of the lipase onto a support material may provide several advantages. For instance, the immobilization gives the lipases higher stability, so they last longer. It also makes their recovery much easier and their reuse possible, which dramatically lowers their cost. Also, the esterification reactions are easier to manipulate when an immobilized enzyme is involved and the lipase becomes susceptible to continuous processes which may also be vital for enzymatic industrialization processes. Sometimes, immobilization leads to improvements in the performance of enzymes. Finally, the dispersion of the lipase on the surface of the support material should ensure the exposure of the lipase to the substrates, leading to dramatic increase in activity of the enzyme per weight unit and considerable cut in dosage of enzyme and thus the cost involved.

If it is desired to prepare a refined fish oil composition enriched with both EPA and DHA then it is preferred to use a lipase which is substantially inactive towards both these n-3 polyunsaturated fatty acids, i.e. which does not significantly discriminate between EPA and DHA. Preferably there is used in this case *Pseudomonas fluorescens* and Pseudomonas sp. lipases, the latter being especially preferred. These lipases are available from Amano International Enzyme Co of Nagoya, Japan.

It is a critical feature of the present process that the lipase-catalysed transesterification should be conducted under substantially anhydrous reaction conditions. Preferably, the total amount of water in the reaction system, from all sources including the marine oil and the lipase, should be less than 1% w/w, preferably less than 0.5% w/w, and most desirably between 0.01–0.25% w/w. (In a typical case the marine oil starting material will contain 0.1–0.2% w/w water, absolute ethanol used as the alcohol reagent will contain 0.2–0.5% w/w water and the lipase preparation will contain 2–2.5% w/w water.)

However, it is not feasible to employ totally anhydrous reaction conditions since a small amount of water, generally about 1–2% by weight based on the weight of the lipase is always required in an enzyme system to establish activity, but depending very much upon the enzyme in question (*Candida cylindrica* lipase, for example, requires the addition of about 10% by weight of water in order to exhibit optimum activity in the present process). As shown in the Examples hereafter, these very small quantities of water do not lead to any significant hydrolysis, and it is possible to keep the concentration of free fatty acids in the transesterified product to below 3% by weight, i.e. only about 10% of the hydrolysis rate reported by Zuyi and Ward, supra.

Another critical feature of the present invention is that the amount of alcohol present should be restricted to not more than 15 molar equivalents, preferably not more than 9 molar equivalents, based on the triglycerides present, (i.e. 3 molar equivalents of alcohol is a stoichiometric quantity). The alcohol thus serves primarily as a reactant, rather than as a solvent. It is surprising that the lipase-catalyzed selective transesterification of the marine oil triglycerides occurs so successfully in such an essentially solvent-free reaction system. Preferably, a substantially stoichiometric quantity of the alcohol is employed, i.e. from 2 to 5 molar equivalents based on triglycerides present, since amounts of alcohol much in excess of the stoichiometric quantity lead to a lower recovery of the desired polyunsaturated fatty acids.

Although it is possible to utilize any $C_1$–$C_6$ alcohol, the use of absolute ethanol (typically with a water content in the range of 0.1–0.5% by weight) is preferred, for reasons of availability and cost, and bearing in mind also the requirement for substantially anhydrous reaction conditions.

The temperature at which the transesterification reaction is conducted is also not critical. However, it is found that the selectivity of the reaction decreases with increasing temperature, although the reaction rate increases. It is generally preferred to carry out the reaction at a temperature not in excess of 40°–60° C., depending on the lipase being employed, more preferably at room temperature (about 20° C.).

The transesterification may be conducted using supercritical fluids, e.g. supercritical $CO_2$, as the reaction medium. For example, ethanolysis of fish oil has been conducted in supercritical $CO_2$ at 250 bar at 40° C. The supercritical $CO_2$ fluid can be used not only as a reaction medium but also to separate the esters and free fatty acids from the residual glycerides.

The lipase-catalyzed transesterification of marine oil triglycerides in accordance with this invention can be schematically illustrated by the following, simplified, reaction equation, using ethanol as the illustrative $C_1$–$C_6$ alcohol.

Step (a)

where $R_1$, $R_2$, $R_3$ indicate the mixed fatty acids (saturated, monounsaturated and polyunsaturated) present, as triglycerides, in the original composition R' indicates n-3 polyunsaturated fatty acids and R" indicates saturated and monounsaturated fatty acids (for simplification only 1,2- and 2,3-diglycerides and 2-monoglycerides are shown on the product side).

The separation of the ethyl ester fraction from the glyceride fraction is suitably carried out by a molecular distillation technique, whereby the relatively volatile ethyl esters can be readily removed from the less volatile residual glyceride mixture. Since the product of the transesterification reaction contains only small quantities of free fatty acids, as a consequence of the use of substantially anhydrous reaction conditions, there can be obtained following the molecular distillation a residual fraction which is substantially free of the unwanted saturated and monounsaturated fatty acids. Even though the molecular distillation step may result in a small part of the most volatile monoglycerides appearing in the distillate, these will be predominantly monoglycerides of relatively short-chain fatty esters (i.e. little or no EPA or DHA is lost into the distillate). Similarly a small part of the ester fraction with low volatility may remain with the residual glyceride mixture i.e. esters of predominantly long-chain fatty acids such as EPA and DHA. Accordingly, part of the relatively small amount of the desired polyunsaturated fatty acids that have participated in the transesterification will nonetheless remain in the residual fraction following distillation. Thus, even though molecular distillation is not usually regarded as being suitable for difficult separations, in our process it has proved to be surprisingly advantageous.

Since environmental pollutants such as pesticides and polychlorinated biphenyls (PCBs) are more volatile than glycerides of long chain fatty acids, molecular distillation will remove these compounds from the glyceride fraction whilst they will become concentrated in the distillate (ester fraction). This is yet another advantage of the use of molecular distillation in the present process.

Indeed, in a specific aspect the present invention provides a process for the removal of environmental pollutants from an oil composition containing saturated and unsaturated fatty acids in the form of triglycerides, which process comprises the steps of:

(a) subjecting the oil composition to a transesterification reaction with a $C_1$–$C_6$ alcohol under substantially anhydrous conditions and in the presence of a lipase active to preferentially catalyze the transesterification of the saturated and monounsaturated fatty acids, the amount of said $C_1$–$C_6$ alcohol present in the reaction being not more than 15 molar equivalents based on the triglycerides present; and thereafter (b) subjecting the product obtained in step (a) to one or more molecular distillations to recover a fraction enriched in glycerides of polyunsaturated fatty acids and from which environmental pollutants have been preferentially removed.

The process of the present invention is particularly adapted to the preparation of compositions containing high concentrations, above 40% by weight, preferably above 70% by weight, of EPA and DHA from marine sources. Since the product of the lipase-catalyzed transesterification contains the unwanted saturated and monounsaturated fatty acids predominantly in the form of their ethyl esters (if ethyl alcohol is used) rather than as free acids (the polyunsaturated fatty acids remain substantially as glycerides), the saturated fatty acid fraction can be removed by a relatively gentle molecular distillation, with a relatively low loss of the desired polyunsaturated fatty acid component. At the same time, relative volatile environmental pollutants such as pesticides and PCBs will be removed with the ethyl ester fraction, as discussed above. Compared with conventional processes for manufacturing EPA/DHA concentrates, the present invention, particularly in its preferred embodiments, thus permits significant advantages, amongst which can be mentioned:

(i) the absence of any solvent leads to a considerable reduction in bulkiness, which effect is enhanced by the ability to use only stoichiometric concentrations of alcohol, (ii) the transesterification reaction can be conducted under mild e.g. room temperature conditions, minimizing side reactions and not requiring high energy inputs, (iii) the recovery of EPA and DHA is very high, and the recovered product is essentially freed of contamination by environmental pollutants, and (iv) the substantially anhydrous reaction conditions used means that there is minimum hydrolysis, whereby molecular distillation of the glyceride fraction from the transesterification reaction gives a good separation of desired polyunsaturated fatty acids from unwanted saturated and monounsaturated fatty acids.

Thus, the alcoholysis process of the present invention can be an initial stage in an integrated production process for the manufacture of an EPA+DHA concentrate. In such an integrated process, following molecular distillation, or other technique, to effect the separation of the saturated fatty acid ethyl ester fraction from the polyunsaturated fatty acid glyceride fraction, the latter fraction, containing the desired polyunsaturated fatty acids can be further treated in order to increase the concentration of particular acids present. For instance, if it is desired to obtain a highly concentrated EPA-plus DHA-containing ethyl ester composition then the glyceride fraction obtained following the molecular distillation can, for instance, be esterified by chemical transesterification with absolute ethanol in the presence of a catalytic amount of for example sodium ethoxide or potassium ethoxide. This process is schematically illustrated by the following reaction equation:

(For simplification, only 1,2- and 2,3-diglycerides and 2-monoglycerides are shown above).

The glycerol produced can then be removed using known techniques. Typically, this will lead to a content of EPA+DHA of approximately 45–50% by weight, with a very good recovery of the polyunsaturated fatty acids, as compared with a conventional process.

More particularly, a preferred integrated process for obtaining a high concentration EPA+DHA composition in accordance with the present invention comprises the following further steps:

(c) transesterifying the glyceride fraction with a lower alcohol, e.g. ethanol, using either chemical catalysis e.g. an alkaline environment containing amounts of a base such as sodium or potassium ethoxide sufficient only to catalyze the transesterification, or enzymatic catalysis e.g. using *Candida antarctica* lipase under substantially anhydrous conditions;

(d) heating the resulting alkyl ester product with an excess of urea in an alkanol to a temperature of from 55° to 99° C.;

(e) cooling the product of step (d), e.g. to about 0°–25° C. to precipitate urea fatty acid alkyl ester adduct and thereafter separating off said adduct to leave a solution mainly containing n-3 fatty acid esters;

(f) separating from the solution remaining from step (e) the n-3 fatty acid alkyl esters; and (g) removing any solvent from the mixture obtained in step (f).

In a particularly preferred embodiment of this integrated process the concentrate obtained in step (g) is further concentrated by means of one or more e.g. nine steps of molecular distillation in order to increase the EPA plus DHA concentration therein to 85% by weight, or higher.

Figure 1:
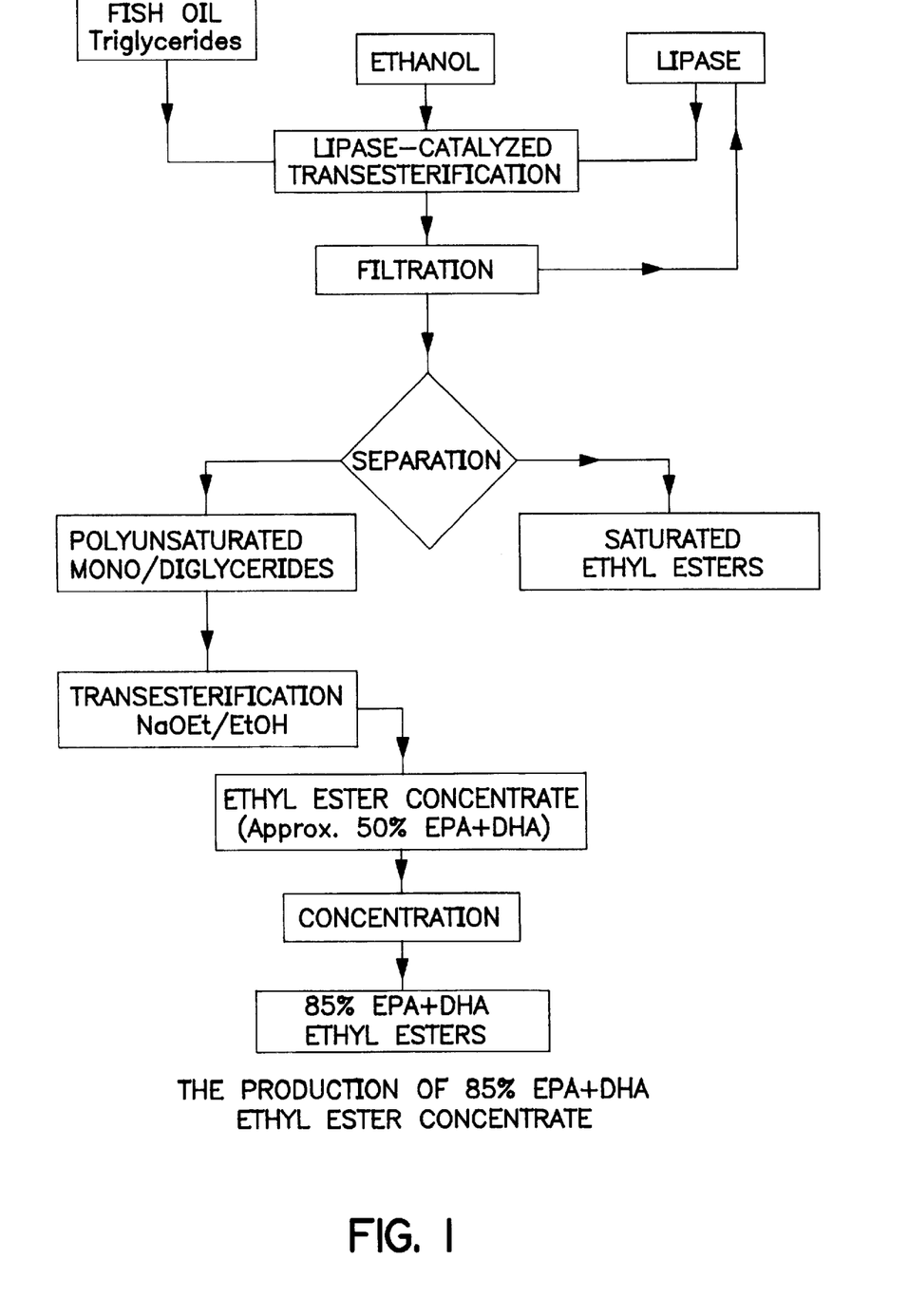
FIG. 1 schematically illustrates an integrated production process in accordance with the present invention for the production of an 85% by weight EPA+DHA ester concentrate.

FIG. 1 of the accompanying drawings schematically illustrates such an integrated production process in accordance with the present invention for the production of an 85% by weight EPA+DHA ethyl ester concentrate.

As an alternative to chemical transesterification of the glyceride fraction e.g. with ethanol in the presence of a catalytic amount of sodium or potassium ethoxide, this transesterification may be effected enzymatically e.g. using *Candida antarctica* lipase. This lipase is quite active towards n-3 polyunsaturated fatty acids as well as other fatty acids, and can be employed to effect the transesterification of the glyceride fraction in a highly efficient manner under mild conditions and in the absence of solvent, thereby contributing to a further reduction in bulkiness.

Figure 2:
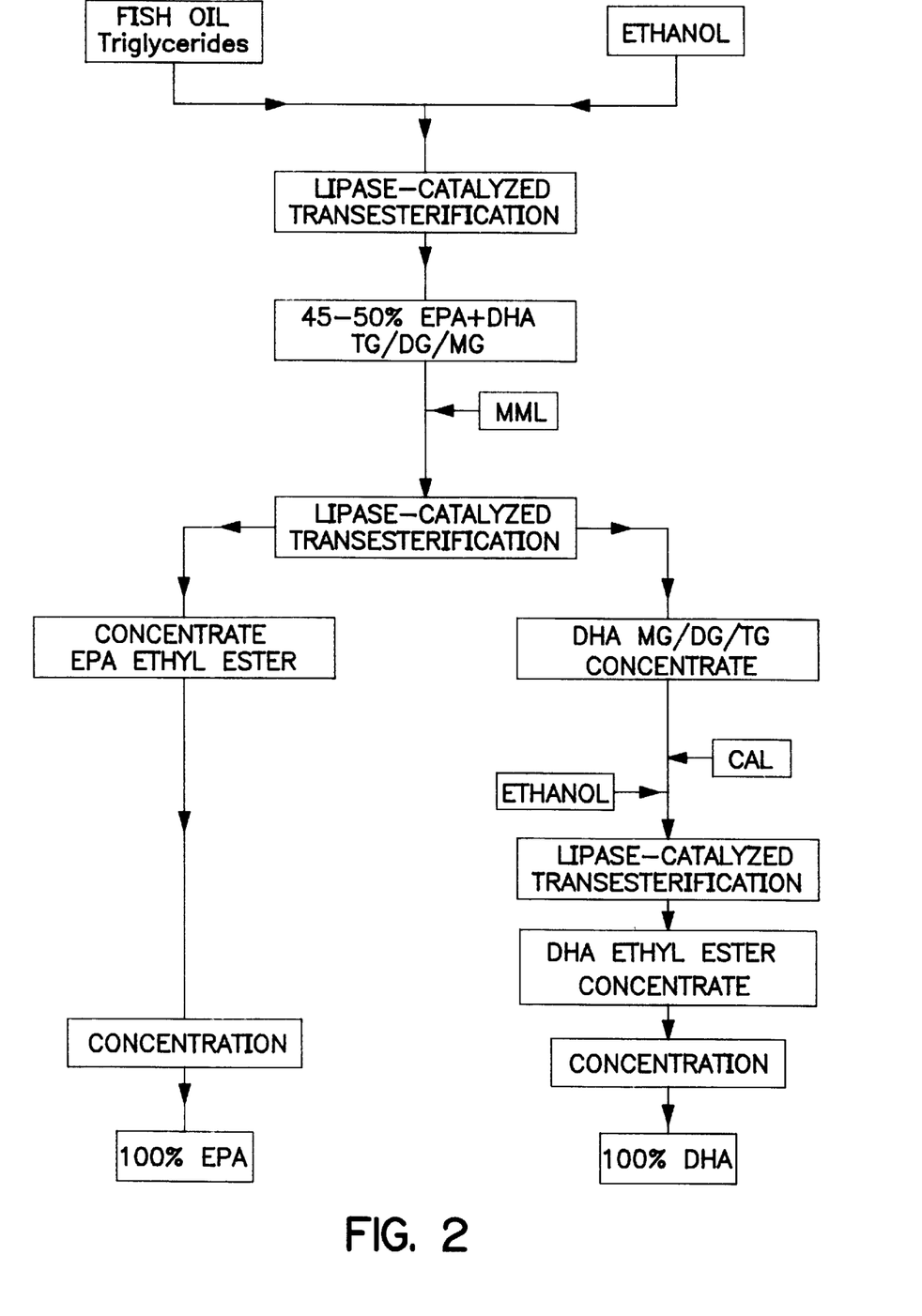
FIG. 2 schematically illustrates an integrated production process in accordance with the present invention for the production of substantially 100% EPA and 100% DHA.

In some instances, it may be desired to isolate a substantially pure single unsaturated fatty acid from the starting marine oil composition. Such a process, for the production of, separately, substantially 100% EPA and 100% DHA is schematically illustrated in FIG. 2 of the accompanying drawings. This embodiment of the invention utilizes not only a Pseudomonas lipase (PSL) to achieve an initial separation of saturated and unsaturated fatty acids in accordance with the teachings of this invention, but also, in subsequent steps *Mucor miehei* lipase (MML) which selectively favours the esterification of EPA, rather than DHA, thereby permitting a good separation of these two acids, and *Candida antarctica* lipase (CAL) to effect the ethanolysis of the DHA-enriched glyceride mixture thereby produced.

More particularly, a preferred integrated process in accordance with this invention for obtaining substantially pure EPA and substantially pure DHA comprises the following steps:

(i) transesterifying the starting marine oil with ethanol using PSL under substantially anhydrous reaction conditions as described above;

(ii) subjecting the lipase-catalyzed transesterification product to molecular distillation to recover a glyceride fraction containing 40–50% EPA plus DHA;

(iii) transesterifying the glyceride fraction from (ii) with ethanol using the *Mucor miehei* lipase (MML) under similar transesterification conditions as for the initial transesterification (i.e. substantial absence of both solvent and water and use of substantially stoichiometric amounts of the ethanol);

(iv) separating the resulting EPA-enriched ethyl ester fraction and the residual DHA-enriched glyceride mixture by molecular distillation in a similar manner to step (ii);

(v) working up the EPA-ethyl ester fraction e.g. by using molecular distillation in combination with urea precipitation, chromatography etc, to concentrate the EPA fraction to substantially 100% purity;

(vi) transesterifying the DHA-enriched glyceride mixture from the MML mediated transesterification recovered from step (iii) with ethanol using *Candida antarctica* lipase (CAL); and (vii) working up the resulting DHA ethyl ester concentrate by similar techniques to those used in step (v), to recover substantially 100% pure DHA.

Although it is a particular advantage of the present invention that it is well adapted to use in integrated processes for the manufacture of compositions having high concentrations of EPA and/or DHA, it is to be noted that the same general techniques can be utilized to isolate other unsaturated fatty acids from marine oil products, e.g. 18:4 n-3, 20:4 n-3, 21:5 n-3 and 22:5 n-3 fatty acids. The process of the invention is applicable to oil products containing polyunsaturated fatty acids from other sources e.g., fermentation products and vegetable and plant oils. The n-6 polyunsaturated fatty acids are characteristic of plant and vegetable oils. n-6 fatty acids of interest include arachidonic acid (AA, 20:4 n-6), bishomo-γ-linolenic acid (BHGLA, 20:3 n-6) and γ-linolenic acid (GLA, 18:3 n-6). Oil products containing arachidonic acid have also been industrially obtained by fermentation using Mortierella.

It has been found it is readily possible to prepare compositions containing at least 40% by weight of arachidonic acid from plant or vegetable oil by the process of the invention. Preferred lipases for use in the process are Pseudomonas sp. lipase and *Pseudomonas fluroescens* lipase. The arachidonic acid fraction may be further concentrated to substantially 100% purity.

Generally, the marine oil composition which is used as the starting material in the process of the present invention may be any raw or partially treated oil from fish or other marine sources and which contains fatty acids, including polyunsaturated fatty acids, in the form of triglycerides. Typically, each triglyceride molecule in such a marine oil will contain, more or less randomly, different fatty acid ester moieties, be they saturated, monounsaturated or polyunsaturated, or long chain or short chain.

The present invention is illustrated by the Examples which follow:

EXAMPLE 1

The purpose of this experiment was to test the use of a number of lipases in a process for separating polyunsaturated fatty acids, particularly EPA and DHA, from saturated and monounsaturated fatty acids in a fish oil composition.

The following lipases were tested:

| Name | Abbreviation | State | Supplier |
|---|---|---|---|
| Mucor miehei | MML | immobilized | Novo |
| Candida antartica | CAL | immobilized | Novo |
| Candida cylindracea | CCL | powder | Sigma |
| Pseudomonas fluorescens | PFL | powder | Amano |
| Penicillium rogueforti | PRL | powder | Amano |
| Pseudomonas sp. | PSL | powder | Amano |

In one test, each of the above lipases was tested at 37° C., and the results are reported in Table I. In another test, the two Pseudomonas lipases, PFL and PSL, were tested at 20° C., and the results are given in Tables II and III.

The procedures used in the tests were as follows:

Fish oil triglycerides were provided by Pronova Biocare a.s., Norway, and contained 14.9% EPA and 9.8% DHA. They were used directly as provided without any further treatment. All solvents were analytical grade and purchased from Merck AG in Germany. Stoichiometric amount of ethanol (absolute) was used, i.e. 3 molar equivalents based on the triglycerides, unless otherwise stated. Except in the case of using Candida cylindracea lipase, no water was added to the reaction system. It is calculated that the water content, arising from the fish oil triglyceride starting material and the lipase, was of the order of 0.3–0.4% by weight. In the case of Candida cylindricea lipase, water was added in an amount of 10% by weight based on the weight of the lipase, resulting in the reaction system containing about 0.8% by weight water in total, i.e. even in this case substantially anhydrous conditions were maintained.

Fatty acid analyses were performed on methyl esters employing a Perkin-Elmer 8140 Gas Chromatograph using a 30 meter capillary column, DB-225 30N 0.25 mm with hydrogen gas as a carrier gas according to a previously described procedure (G.G. Haraldsson and Ö. Almarsson, Acta Chemica Scandinavica, 1991, 45, 723–730). For the detailed investigation represented in Tables II and III for PSL and PFL, respectively, preparative thin-layer chromatography was employed to separate the lipid fractions from the reaction mixture at appropriate time intervals to monitor the progress of the reactions. Silica gel plates from Merck (Art 5721) were used after washing with a 50:50 mixture of chloroform-methanol and heating at 110° C. for 30 min. Elution was performed with 80:20:1 mixture of petroleum ether-diethyl ether-acetic acid. Rhodamine 6G (Merck) was used to visualize the bands which subsequently were scraped off and the fat methylated and analyzed as quoted above. Methyl esters of $C_{19:0}$ or $C_{21:01}$ purchased from Sigma, were added to the samples as internal standards before injection.

In the experiments reported in Table I separation of ethyl esters and glycerides were performed on a Waters PrepL™ System 500A instrument. The PrepPak® 500/Silica Cartridge column from Millipore was eluted with 10% ethyl ether in petroleum ether at the flow rate of 250 ml/min. Each run afforded two peaks according to the index of refraction detector, the first appearing after approximately one column volume and consisting of pure ethyl esters and the second one eluting after roughly two column volumes containing pure triglycerides according to TLC. The remaining mono- and diglycerides were washed off the column by methanol.

In a typical procedure the lipase (0.5 g) was added to a mixture of the fish oil (5.0 g, approximately 5.67 mmol (M.wt. appr. 882 g/mol)) and absolute ethanol (0.80 g, 17.4 mmol). The resulting enzyme suspension was gently stirred at room temperature (37° C. for the experiments in Table I) under nitrogen. After appropriate time the reaction was discontinued by chloroform addition and separation of the enzyme by filtration. The organic solvent was removed in vacuo (rotary evaporator and high-vacuum pump treatment) to afford the crude product mixture in quantitative yields. The product was dissolved in equal volume of chloroform and injected into the HPLC instrument as was described above. Each fraction was collected and the solvent evaporated off in vacuo, weighed and finally analyzed by gas chromatography.

When preparative TLC was used instead of preparative HPLC small samples (100–200 mg) were withdrawn from the reaction mixture by the aid of a Pasteur pipette at appropriate time. Enzyme particles were separated by filtering the sample through a cotton wool plug located inside a second Pasteur pipette. Each sample was then diluted in chloroform (250 mg/ml) before introducing it to the TLC plate.

The results are presented in Tables I–III below:

The first table, Table I, summarizes the results of experiments conducted at 37° C. (using 3 molar equivalents of ethanol) with all the lipases tested:

TABLE I

| MML (10%*, 23 hours) | | EPA | | DHA | |
|---|---|---|---|---|---|
| Fraction | % wt | % comp. | % recovery | % comp. | % recovery |
| EE | 32.0 | 8.73 | 18.66 | 0.96 | 3.13 |
| TG | 35.0 | 20.12 | 47.04 | 11.49 | 41.14 |
| MG/DG | 32.0 | 16.07 | 34.35 | 17.01 | 55.70 |
| MG/DG/TG | 67.0 | 18.19 | 81.39 | 14.12 | 96.84 |

| CAL (2%*, 10 hours) | | EPA | | DHA | |
|---|---|---|---|---|---|
| Fraction | % wt | % comp. | % recovery | % comp. | % recovery |
| EE | 47.3 | 18.51 | 54.51 | 4.33 | 20.36 |
| TG | 33.8 | 15.56 | 32.74 | 12.45 | 41.84 |
| MG/DG | 18.9 | 10.83 | 12.74 | 20.11 | 37.79 |
| MG/DG/TG | 52.7 | 13.86 | 45.49 | 15.20 | 79.64 |

| CAL (2%*, 23 hours) | | EPA | | DHA | |
|---|---|---|---|---|---|
| Fraction | % wt | % comp. | % recovery | % comp. | % recovery |
| EE | 69.5 | 17.28 | 76.45 | 6.77 | 44.11 |
| TG | 16.6 | 13.16 | 13.91 | 14.73 | 22.92 |
| MG/DG | 13.9 | 10.90 | 9.64 | 25.30 | 32.97 |
| MG/DG/TG | 30.5 | 12.13 | 23.55 | 19.55 | 55.89 |

| CCL (10%*, 71 hours) | | EPA | | DHA | |
|---|---|---|---|---|---|
| Fraction | % wt | % comp. | % recovery | % comp. | % recovery |
| EE | 5 | 6.52 | 2.17 | 2.73 | 1.45 |
| TG | 69 | 16.19 | 74.53 | 10.81 | 79.00 |
| MG/DG | 26 | 13.43 | 23.30 | 7.1 | 19.55 |
| MG/DG/TG | 95 | 15.43 | 97.83 | 9.79 | 98.55 |

| PRL (10%*, 102 hours) | | EPA | | DHA | |
|---|---|---|---|---|---|
| Fraction | % wt | % comp. | % recovery | % comp. | % recovery |
| EE | 8.4 | 7.70 | 4.12 | 2.48 | 2.14 |
| TG | 61 | 17.08 | 66.37 | 10.53 | 65.90 |

TABLE I-continued

| | | | | | |
|---|---|---|---|---|---|
| MG/DG | 30.6 | 15.14 | 29.51 | 10.18 | 31.96 |
| MG/DG/TG | 91.6 | 16.43 | 95.88 | 10.41 | 97.86 |

| | | EPA | | DHA | |
|---|---|---|---|---|---|
| PSL (10%*, 5 hours) | | % | % | % | % |
| Fraction | % wt | comp. | recovery | comp. | recovery |
| EE | 40.3 | 2.42 | 6.00 | 2.92 | 11.70 |
| TG | 11.5 | 30.87 | 21.84 | 13.53 | 15.47 |
| MG/DG | 48.2 | 24.34 | 72.16 | 15.20 | 72.83 |
| MG/DG/TG | 59.7 | 25.60 | 94.00 | 14.88 | 88.30 |

| | | EPA | | DHA | |
|---|---|---|---|---|---|
| PFL (10%*, 10 hours) | | % | % | % | % |
| Fraction | % wt | comp. | recovery | comp. | recovery |
| EE | 36 | 2.87 | 6.44 | 2.39 | 8.48 |
| TG | 17.7 | 28.23 | 31.13 | 11.41 | 19.90 |
| MG/DG | 46 | 21.78 | 62.43 | 15.8 | 71.62 |
| MG/DG/TG | 63.7 | 23.57 | 93.56 | 14.58 | 91.52 |

*Percentages refer to the dosage of lipase based on the weight of triglycerides

The results for *Candida cylinracea* (CCL) are with 10% water added, based on the lipase, since this lipase was inactive without water addition. The poor selectivity of *Candida antarctica* lipase (CAL) towards EPA and DHA will be noted, and accordingly this lipase is not useful in this invention. In contrast, all the other lipases tested showed satisfactory activity and selectivity, and the two Pseudomonas species lipases were outstanding in these respects.

TABLE II

PSL with 3 molar equivalents of ethanol at 20° C.

| Class | 1 h | 2 h | 4 h | 8 h | 13 h | 24 h |
|---|---|---|---|---|---|---|
| Wt % of lipid classes | | | | | | |
| MG | 5.0 | 9.4 | 13.0 | 17.9 | 16.8 | 15.9 |
| DG | 29.1 | 35.6 | 31.6 | 23.3 | 24.9 | 25.9 |
| FFA | 2.6 | 2.9 | 2.5 | 2.7 | 2.7 | 2.7 |
| TG | 42.9 | 17.9 | 14.2 | 9.1 | 7.5 | 3.7 |
| EE | 20.4 | 34.2 | 38.7 | 47.0 | 48.1 | 51.8 |
| Area % EPA | | | | | | |
| MG | 12.0 | 12.8 | 16.4 | 19.2 | 22.5 | 26.1 |
| DG | 19.3 | 21.6 | 26.0 | 28.1 | 32.3 | 32.3 |
| FFA | 3.0 | 2.7 | 5.0 | 6.2 | 5.7 | 9.0 |
| TG | 19.2 | 23.2 | 30.3 | 31.8 | 32.7 | 32.0 |
| EE | 1.1 | 1.2 | 1.6 | 2.0 | 2.2 | 2.8 |
| MG/DG/TG | 18.8 | 20.7 | 24.9 | 25.6 | 29.0 | 30.1 |
| Area % DHA | | | | | | |
| MG | 15.5 | 16.2 | 16.4 | 17.3 | 18.4 | 17.7 |
| DG | 12.7 | 13.2 | 13.7 | 14.1 | 15.1 | 14.9 |
| FFA | 2.5 | 2.7 | 4.9 | 6.4 | 6.7 | 9.9 |
| TG | 9.8 | 10.3 | 11.6 | 12.2 | 12.9 | 12.3 |
| EE | 1.5 | 1.4 | 1.9 | 2.4 | 2.8 | 3.6 |
| MG/DG/TG | 11.3 | 12.8 | 13.8 | 14.9 | 15.9 | 15.7 |
| Area % EPA + DHA | | | | | | |
| MG | 27.5 | 29.0 | 32.8 | 36.5 | 40.9 | 43.8 |
| DG | 32.0 | 34.8 | 39.7 | 42.2 | 47.4 | 47.2 |
| FFA | 5.5 | 5.4 | 9.9 | 12.6 | 12.4 | 18.9 |
| TG | 29.0 | 33.5 | 41.9 | 44.0 | 45.6 | 44.3 |
| EE | 2.6 | 2.6 | 3.5 | 4.4 | 5.0 | 6.4 |
| MG/DG/TG | 30.0 | 33.6 | 38.7 | 40.5 | 44.9 | 45.8 |

TABLE II-continued

PSL with 3 molar equivalents of ethanol at 20° C.

| Class | 1 h | 2 h | 4 h | 8 h | 13 h | 24 h |
|---|---|---|---|---|---|---|
| Weight % EPA | | | | | | |
| MG | 3.5 | 7.8 | 12.1 | 21.4 | 21.8 | 22.4 |
| DG | 37.2 | 56.5 | 53.5 | 51.3 | 53.1 | 51.7 |
| FFA | 0.6 | 0.7 | 0.9 | 1.2 | 1.2 | 1.6 |
| TG | 57.3 | 32.2 | 29.4 | 20.3 | 17.0 | 15.4 |
| EE | 1.5 | 2.9 | 4.1 | 5.7 | 6.9 | 9.0 |
| MG/DG/TG | 98.0 | 96.5 | 95.0 | 93.0 | 91.9 | 89.5 |
| Weight % DHA | | | | | | |
| MG | 7.5 | 15.6 | 22.8 | 33.0 | 29.9 | 26.2 |
| DG | 40.4 | 55.0 | 48.3 | 38.6 | 41.5 | 41.0 |
| FFA | 0.8 | 1.1 | 1.5 | 2.2 | 2.3 | 3.0 |
| TG | 48.1 | 22.6 | 19.4 | 13.8 | 11.4 | 10.3 |
| EE | 3.3 | 5.7 | 8.0 | 12.4 | 14.8 | 19.6 |
| MG/DG/TG | 96.0 | 93.2 | 90.5 | 85.4 | 82.8 | 77.5 |

Table II above demonstrates that excellent results were obtained with Pseudomonas sp. lipase in the transesterification reaction. Thus, 48% conversion was reached after 13 hours leading to 44.9% EPA+DHA content in the glycerides with 91.9% recovery of EPA and 82.8% recovery of DHA. After 24 hours of reaction, 52% conversion was obtained leading to 45.8% EPA+DHA content in the glycerides with 89.5 and 77.5% recovery, respectively, for EPA and DHA, suggesting that in practice it would be appropriate to stop the reaction at an earlier stage. The extent of the hydrolysis side reaction remained constant, and low, throughout the reaction, being in the range 2.5–2.9%.

TABLE III

PFL with 3 molar equivalents of ethanol at 20° C.

| Class | 1 h | 2 h | 4 h | 8 h | 14 h | 25 h | 49 h |
|---|---|---|---|---|---|---|---|
| Wt % of lipid classes | | | | | | | |
| MG | 2.2 | 2.9 | 4.8 | 10.2 | 15.1 | 18.1 | 16.7 |
| DG | 10.8 | 15.6 | 23.4 | 34.8 | 29.2 | 22.5 | 16.0 |
| FFA | 0.9 | 0.9 | 1.3 | 1.2 | 1.2 | 1.0 | 1.4 |
| TG | 81.9 | 71.0 | 49.1 | 27.3 | 15.8 | 9.9 | 6.3 |
| EE | 4.2 | 9.6 | 21.3 | 26.5 | 38.7 | 48.4 | 59.7 |
| Area % EPA | | | | | | | |
| MG | 11.6 | 12.7 | 13.7 | 12.7 | 14.5 | 16.9 | 21.5 |
| DG | 17.9 | 19.6 | 16.9 | 17.8 | 25.5 | 28.9 | 27.1 |
| FFA | 3.5 | 4.5 | 6.3 | 5.1 | 5.5 | 8.8 | 14.2 |
| TG | 15.9 | 16.4 | 18.0 | 22.0 | 29.2 | 31.8 | 26.7 |
| EE | 0.0 | 1.5 | 1.3 | 1.9 | 2.2 | 3.1 | 4.7 |
| MG/DG/TG | 16.0 | 16.8 | 17.4 | 18.7 | 23.7 | 25.2 | 24.6 |
| Area % DHA | | | | | | | |
| MG | 10.5 | 14.7 | 18.1 | 18.1 | 18.6 | 18.7 | 13.2 |
| DG | 12.2 | 12.9 | 13.5 | 10.9 | 13.8 | 14.4 | 11.8 |
| FFA | 3.4 | 3.5 | 4.3 | 4.4 | 3.2 | 9.4 | 8.4 |
| TG | 9.6 | 9.6 | 9.3 | 9.8 | 10.8 | 11.4 | 10.1 |
| EE | 0.0 | 1.3 | 1.1 | 1.5 | 2.0 | 2.7 | 3.7 |
| MG/DG/TG | 9.9 | 10.3 | 11.1 | 11.5 | 14.2 | 15.4 | 12.1 |
| Area % EPA + DHA | | | | | | | |
| MG | 22.1 | 27.4 | 31.8 | 30.8 | 33.1 | 35.6 | 34.7 |
| DG | 30.1 | 32.5 | 30.4 | 28.7 | 39.3 | 43.3 | 38.9 |
| FFA | 6.9 | 8.0 | 10.6 | 9.5 | 8.7 | 18.2 | 22.6 |
| TG | 25.5 | 26.0 | 27.3 | 31.8 | 40.0 | 43.2 | 36.8 |
| EE | 0.0 | 2.8 | 2.4 | 3.4 | 4.2 | 5.8 | 8.4 |
| MG/DG/TG | 25.9 | 27.2 | 28.5 | 30.2 | 37.9 | 40.5 | 36.8 |
| Weight % EPA | | | | | | | |
| MG | 1.4 | 2.0 | 4.1 | 8.0 | 12.7 | 18.8 | 25.5 |

TABLE III-continued

PFL with 3 molar equivalents of ethanol at 20° C.

| Class | 1 h | 2 h | 4 h | 8 h | 14 h | 25 h | 49 h |
|---|---|---|---|---|---|---|---|
| DG | 12.1 | 19.4 | 28.0 | 43.6 | 49.2 | 46.1 | 35.3 |
| FFA | 0.2 | 0.3 | 0.6 | 0.5 | 0.5 | 0.7 | 1.7 |
| TG | 86.3 | 77.5 | 65.4 | 44.4 | 32.2 | 23.7 | 14.4 |
| EE | 0.0 | 0.9 | 1.9 | 3.5 | 5.5 | 10.6 | 23.0 |
| MG/DG/TG | 99.8 | 98.9 | 97.5 | 96.0 | 94.1 | 88.6 | 75.2 |
| Weight % DHA | | | | | | | |
| MG | 2.0 | 3.8 | 8.5 | 18.5 | 27.1 | 33.7 | 28.1 |
| DG | 13.3 | 20.7 | 35.1 | 44.0 | 44.3 | 36.9 | 27.6 |
| FFA | 0.4 | 0.4 | 0.7 | 0.7 | 0.4 | 1.2 | 1.8 |
| TG | 84.3 | 73.9 | 53.2 | 32.5 | 19.9 | 13.5 | 9.8 |
| EE | 0.0 | 1.3 | 2.5 | 4.4 | 8.2 | 14.7 | 32.6 |
| MG/DG/TG | 99.6 | 98.4 | 96.8 | 95.0 | 91.3 | 84.1 | 65.5 |

Table III above shows that good results in the transesterification are also obtained with *Pseudomonas fluorescens* lipase, although the rate of conversion is rather slower than with PSL. Thus, after 25 hours, 48% conversion was obtained, which increased to 60% after 49 hours. On the other hand, the extent of hydrolysis was somewhat lower. The performance of this lipase is also inferior to that of Pseudomonas sp. lipase in terms of EPA and DHA recovery (88.6% and 84.1%, respectively) and EPA+DHA composition (40.5%) after 25 hours.

In the above Tables I–III the following abbreviations are used:

MG monoglyceride

DG diglyceride

TG triglyceride

FFA free fatty acid

EE ethyl ester

Area % EPA Area % is based on the

Area % DHA integration of the corresponding

Area a EPA+DHA GC-chromatograms

These abbreviations will be used throughout the remaining Examples.

It is clear from the above tables that both the Pseudomonas lipases exhibit uniquely low affinity towards EPA and DHA but high affinity towards the initial triglycerides.

It will also be noted that the two Pseudomonas lipases to some extent tend to favour the transesterification of DHA, rather than EPA. This is most unusual behaviour, since all other lipases which we have tested show the reverse tendency.

It will be further noted from Tables II and III that after a certain time the MG/DG/TG ratio starts to decline from the optimum. Accordingly, it is normally desirable to conclude the transesterification reaction before it has gone to completion.

EXAMPLE 2

This experiment was designed to test the two Pseudomonas lipases PSL and PFL in larger scale runs.

EXAMPLE 2a—PSL

Pseudomonas sp. lipase (100 g, 25 200 activity units/g) was added to a mixture of the fish oil (1000 g, approximately 1.13 mol) and absolute ethanol (170 g, 3.70 mol). The resulting enzyme suspension was gently stirred on a magnetic stirrer at room temperature under nitrogen. The water content of the reaction mixture was calculated to be approximately 0.3–0.4% by weight.

After 25 hours a sample was withdrawn according to the procedure described in Example 1 and analysed. The reaction was allowed to continue for another 24 hours. A centrifuge was employed for separating the reaction mixture and the lipase (5000 rpm for 10 min).

When the reaction was stopped after 50 hours the product had the following composition:

TABLE IV

| 50 hours Lipid Class | EPA % wt | EPA % area | DHA % wt | DHA % area | EPA + DHA % wt | EPA + DHA % area |
|---|---|---|---|---|---|---|
| MG | 17.1 | 17.0 | 18.0 | 17.8 | 28.9 | 34.8 |
| DG | 26.0 | 28.9 | 53.1 | 14.5 | 42.1 | 43.4 |
| FFA | 2.8 | 5.7 | 1.2 | 6.0 | 1.9 | 11.7 |
| TG | 8.9 | 28.8 | 19.3 | 11.8 | 12.2 | 40.6 |
| EE | 46.2 | 2.6 | 8.4 | 2.9 | 14.8 | 5.5 |
| MG/DG/TG | 52.0 | 25.0 | 90.4 | 15.1 | 83.2 | 40.1 |

Part of the product (902.4 g) was degassed under vacuum at 80° C. in order to remove volatile components. The volatile components were collected in a cold trap cooled with liquid nitrogen. After degassing 844.1 g of glyceride/ethyl/ester mixture remained. 756.3 g of this mixture was distilled in a molecular distillation still at 125° C., 0.005 mbar. This gave a distillate of 358.6 g (47.4%) and a residue weighing 388.3 g (51.3%). The fractions had the following composition.

TABLE V

| | TG A % | DG A % | MG A % | EE A % | EPA A % | DHA A % | EPA + DHA A % |
|---|---|---|---|---|---|---|---|
| after de-gassing | 11.2 | 35.5 | 19.7 | 33.6 | 16.4 | 11.0 | 27.4 |
| distillate | — | 0.9 | 10.6 | 88.5 | 3.6 | 3.4 | 7.0 |
| residue | 18.5 | 54.0 | 25.2 | 2.3 | 29.1 | 18.2 | 47.3 |

The table shows that the residue contains 47.3% EPA+DHA, i.e. a higher concentration of these desired n-3 polyunsaturated fatty acids than prior to the molecular distillation (see Table IV). This means that it is ideal for further concentration using known techniques, i.e. urea fractionation followed by molecular distillation.

It should be noted that the distillate contains appreciable amounts of monoglycerides (10.6%), while the residue contains 2.3% ethyl esters. As discussed above, these will predominantly be monoglycerides from relatively short-chain fatty acids and ethyl esters from long-chain fatty acids, respectively.

EXAMPLE 2b 1 kg of the same oil as in Example 2a was transesterified with ethanol using the PFL enzyme. The reaction was stopped after 48 hours. Composition of intermediary product is shown in Table VI.

TABLE VI

| 48 hours Lipid Class | EPA % wt | EPA % area | DHA % wt | DHA % area | EPA + DHA % wt | EPA + DHA % area |
|---|---|---|---|---|---|---|
| MG | 16.2 | 14.3 | 14.0 | 16.4 | 27.3 | 30.7 |
| DG | 26.8 | 26.5 | 48.6 | 13.7 | 43.1 | 40.2 |
| TG | 14.9 | 26.3 | 28.3 | 9.0 | 17.9 | 36.2 |

TABLE VI-continued

| 48 hours Lipid Class | EPA % wt | EPA % area | DHA % wt | DHA % area | EPA + DHA % wt | EPA + DHA % area |
|---|---|---|---|---|---|---|
| EE | 42.2 | 2.9 | 9.9 | 2.4 | 11.6 | 5.3 |
| MG/DG/TG | 57.9 | 23.0 | 90.9 | 13.5 | 88.3 | 36.5 |

The intermediary product was degassed and molecular distilled under the same conditions as in Example 2a. The results are tabulated below.

| | TG A % | DG A % | MG A % | EE A % | EPA A % | DHA A % | EPA + DHA A % |
|---|---|---|---|---|---|---|---|
| after de-gassing | 15.8 | 31.4 | 20.1 | 32.8 | 15.9 | 10.0 | 25.9 |
| distillate | — | — | 13.7 | 86.3 | 4.2 | 2.9 | 7.1 |
| residue | 25.7 | 48.8 | 23.5 | 2.0 | 27.8 | 18.1 | 45.9 |

EXAMPLE 3

The products resulting from three pilot plant runs similar to that of Example 2 were analyzed to determine the level of environmental pollutants. The results are shown in Table VII below:

TABLE VII

Results from three examples (mg/kg):

| | α-BCH | HCB | total DDT | Toxaphene |
|---|---|---|---|---|
| Starting material | nd | nd | 0.03 | nd |
| PSL glyceride product | nd | nd | nd | nd |
| PSL ethyl ester by-product | nd | 0.01 | 0.03 | nd |
| PFL #1 glyceride product | nd | nd | nd | nd |
| PFL #1 ethyl ester by-product | 0.005 | 0.02 | 0.03 | 0.4 |
| PFL #2 glyceride product | nd | nd | nd | nd |
| PFL #3 ethyl ester by-product | nd | 0.03 | 0.03 | 0.4 | nd = not detected
HCH = hexachlorocyclohexane
HCB = hexachlorobenzene
DDT = dichlorodiphenyltrichloroethane The above results show that the pollutants are concentrated in the ethyl ester fractions. For some of the pesticides, the levels in the starting material obviously were just below the detection limit of the analytical method. This is the reason why we detected these pesticides in the ethyl ester fractions but not in the original fish oil. Strangely, the DDT level does not seem to increase in the ethyl ester fraction compared to the original oil. Before we separated the ethyl esters and glycerides (by molecular distillation) we performed a gentle molecular distillation step in order to strip the reaction mixture of unreacted ethanol. Evidently this ethanol stripping was sufficient to remove part of the DDT. Analysis of the recovered ethanol (example PSL) showed total DDT of 0.03 mg/kg, while none of the other pesticides could be detected.

EXAMPLE 4

The purpose of this experiment was to compare different procedures for immobilising lipases and to investigate the effect of using lipases in an immobilised form in the process of the invention.

A. Immobilisation Procedures (i) PSL and PFL immobilisation on Duolite

Duolite A 562 (Duolite International; 10.0 g) was washed 3–4 times with 30 mM NaOH (250 ml each time) on a Buchner funnel and then placed into a 150 ml beaker together with water (40 ml) and a magnetic follower. The pH of that solution was adjusted to pH 8 by the aid of an autotitrator (1.00 M NaOH). If the initial pH is below pH 5.0 it may take considerable time to reach equilibrium at pH 8. If the pH on the other hand is above pH 8.0 it does not drop until the lipase solution is added. The lipase (2.0 g, PSL/PFL) dissolved in water (20 ml) was added to the Duolite solution via a Pasteur pipette. With the aid of the autotitrator the pH was maintained between pH 8.0–8.4 during the addition and the solution was magnetically stirred for 1 hour. After that time 95–99% lipase had been immobilised on the Duolite. After stirring, the lipase preparation was washed with a buffer solution (Tris-HCl; pH 8.0). Finally, the immobilised lipase preparation was dried in vacuo (0.1–0.01 mmHg) for 0.5–1 hour. A steam bath (40° C.) may be used to speed up the drying process. The immobilised lipase preparation was stored in a refrigerator (4° C.).

(ii) PSL immobilisation on Amberlite

Amberlite XAD-7 resin (50 g; Rohm and Haas; 70% water-content) was thoroughly washed with 0.1 M sodium phosphate buffer at pH 7.0 (twice with 125 ml). PSL powder (Amano AK; 1.5 g; 20,000 lipase units (LU, defined as $\mu$mol of free fatty acids produced in one minute as based on tributyrin hydrolysis; 17 LU/mg powder) was dissolved in 0.1 M sodium phosphate buffer at pH 7.0 (200 ml). When a drop in pH occurred, pH was adjusted to 7.0. The lipase solution was then added to the resin and the resulting suspension stirred until at least 95% of immobilisation had taken place (about 1 hour) as established by activity measurement of the supernatant liquid by tributyrin hydrolysis.

(iii) Activity measurement of immobilised lipase Preparations

The immobilised resin (about 40 mg) was accurately weighed and added to n-butyl palmitate (310–315 mg). To that mixture was added 95% ethanol (120 $\mu$l) and the mixture stirred well for 90 min. A sample was collected and analyzed by GLC. The amount of lipase alcohol units (LAU) is defined as the amount of ethyl palmitate ($\mu$mol) produced in one min.

B. Productivity Experiments with Immobilised PSL

Fish oil ethanolysis productivity experiments for PSL immobilised on both Duolite and Amberlite were carried out according to the following method.

(i) Productivity experiments with immobilised PSL

Fish oil (100 g), absolute ethanol (20 ml) and water (1 ml) were mixed together and the resulting mixture vigorously stirred until a good dispersion had formed. The moisture-free immobilised lipase (log) was added to the dispersion, which was vigorously agitated until a clear solution had formed. Then, the mixture was stirred gently, until a conversion of approximately 50% had been reached (24 hours). The lipase was separated off by filtration and used in the successive runs, whereas the fat was analysed as described earlier.

The results of the productivity experiments with PSL immobilised on Duolite are given in Table VIII.

TABLE VIII

Productivity experiments with PSL on Duolite.

| Class | Run 1 | Run 2 | Run 3 | Run 4 | Run 5 |
|---|---|---|---|---|---|
| Weight % of Lipid Classes | | | | | |
| EE | 46.1 | 51.0 | 51.7 | 49.2 | 46.9 |
| FFA | 4.5 | 4.4 | 5.0 | 4.1 | 5.6 |
| MG | 15.9 | 16.8 | 17.3 | 16.5 | 17.0 |
| DG | 26.3 | 22.8 | 21.3 | 25.2 | 25.1 |
| TG | 7.3 | 5.1 | 4.7 | 5.0 | 5.5 |
| MG/DG/TG | 49.5 | 44.7 | 43.3 | 46.7 | 47.6 |
| Area % EPA | | | | | |
| EE | 1.6 | 1.9 | 1.9 | 1.8 | 1.8 |
| FFA | 7.6 | 8.9 | 9.8 | 6.8 | 6.9 |
| MG | 26.5 | 26.5 | 25.1 | 23.7 | 22.9 |
| DG | 42.0 | 37.6 | 37.1 | 35.3 | 35.7 |
| TG | 41.0 | 35.8 | 35.2 | 35.6 | 42.7 |
| MG/DG/TG | 36.9 | 33.2 | 32.1 | 31.2 | 31.9 |
| Area % DHA | | | | | |
| EE | 1.9 | 2.3 | 2.3 | 2.2 | 2.1 |
| FFA | 9.3 | 10.8 | 9.8 | 8.1 | 18.4 |
| MG | 20.2 | 20.0 | 19.8 | 18.0 | 18.5 |
| DG | 17.5 | 15.6 | 15.0 | 14.6 | 14.5 |
| TG | 15.5 | 12.5 | 13.2 | 12.7 | 13.9 |
| MG/DG/TG | 18.1 | 16.9 | 16.7 | 15.6 | 15.9 |
| Area % EPA + DHA | | | | | |
| EE | 3.5 | 4.2 | 4.2 | 4.0 | 3.9 |
| FFA | 16.9 | 19.7 | 19.6 | 14.9 | 25.3 |
| MG | 46.7 | 46.5 | 44.8 | 41.7 | 41.4 |
| DG | 59.6 | 53.2 | 52.1 | 49.8 | 50.2 |
| TG | 56.5 | 48.4 | 48.3 | 48.3 | 56.5 |
| MG/DG/TG | 55.0 | 50.1 | 48.8 | 46.8 | 47.8 |
| Weight % EPA | | | | | |
| EE | 3.8 | 6.1 | 6.4 | 5.7 | 5.1 |
| FFA | 2.0 | 2.7 | 3.6 | 2.0 | 2.6 |
| MG | 19.1 | 24.3 | 25.0 | 21.9 | 20.8 |
| DG | 57.9 | 54.3 | 52.8 | 57.7 | 55.5 |
| TG | 17.1 | 12.6 | 12.2 | 12.7 | 16.0 |
| MG/DG/TG | 94.2 | 91.2 | 90.0 | 92.3 | 92.3 |
| Weight % DHA | | | | | |
| EE | 8.7 | 13.2 | 14.1 | 12.7 | 10.6 |
| FFA | 4.7 | 5.9 | 6.3 | 4.4 | 12.1 |
| MG | 27.9 | 32.7 | 34.2 | 30.7 | 29.1 |
| DG | 46.4 | 40.3 | 37.5 | 43.8 | 39.2 |
| TG | 12.4 | 7.9 | 8.0 | 8.4 | 9.0 |
| MG/DG/TG | 86.7 | 80.8 | 79.6 | 82.9 | 77.3 |

| Class | Run 6 | Run 7 | Run 8 | Run 9 | Run 10 |
|---|---|---|---|---|---|
| Weight % of Lipid Classes | | | | | |
| EE | 55.4 | 53.7 | 54.9 | 48.3 | 48.9 |
| FFA | 2.5 | 2.3 | 3.0 | 3.6 | 4.4 |
| MG | 16.5 | 14.7 | 13.5 | 16.7 | 14.6 |
| DG | 23.7 | 27.4 | 26.1 | 25.5 | 25.9 |
| TG | 1.8 | 1.9 | 2.5 | 5.9 | 6.2 |
| MG/DG/TG | 42.0 | 44.0 | 42.1 | 48.1 | 46.7 |
| Area % EPA | | | | | |
| EE | 1.7 | 1.9 | 1.6 | 1.4 | 1.4 |
| FFA | 11.2 | 11.8 | 11.1 | 8.2 | 7.7 |
| MG | 22.4 | 19.5 | 17.4 | 20.9 | 21.6 |
| DG | 35.1 | 36.7 | 34.2 | 36.3 | 38.7 |
| TG | 29.1 | 31.7 | 34.8 | 44.4 | 42.6 |
| MG/DG/TG | 29.9 | 30.7 | 30.0 | 32.0 | 33.9 |
| Area % DHA | | | | | |
| EE | 1.9 | 2.2 | 1.8 | 1.5 | 1.6 |
| FFA | 18.8 | 20.6 | 21.5 | 9.0 | 7.7 |
| MG | 15.4 | 16.3 | 14.9 | 17.6 | 18.9 |
| DG | 13.2 | 15.0 | 14.1 | 15.1 | 16.1 |
| TG | 9.8 | 10.7 | 11.7 | 14.2 | 14.0 |
| MG/DG/TG | 13.9 | 15.3 | 14.2 | 15.9 | 16.7 |
| Area % EPA + DHA | | | | | |
| EE | 3.6 | 4.1 | 3.4 | 2.9 | 3.0 |
| FFA | 30.0 | 32.4 | 32.6 | 17.2 | 15.4 |
| MG | 37.8 | 35.7 | 32.1 | 38.5 | 40.5 |
| DG | 48.3 | 51.7 | 48.3 | 51.4 | 54.7 |
| TG | 38.9 | 42.4 | 46.6 | 58.7 | 56.6 |
| MG/DG/TG | 43.8 | 45.8 | 44.2 | 47.9 | 50.6 |
| Weight % EPA | | | | | |
| EE | 7.1 | 7.0 | 6.8 | 4.1 | 4.1 |
| FFA | 2.3 | 2.1 | 2.8 | 2.0 | 2.2 |
| MG | 23.9 | 17.0 | 15.3 | 18.7 | 16.4 |
| DG | 62.4 | 69.3 | 67.9 | 57.4 | 60.0 |
| TG | 4.4 | 4.6 | 7.3 | 17.7 | 17.4 |
| MG/DG/TG | 90.6 | 90.9 | 90.5 | 93.8 | 93.7 |
| Weight % DHA | | | | | |
| EE | 15.0 | 14.4 | 13.1 | 8.8 | 8.9 |
| FFA | 7.3 | 6.5 | 9.6 | 4.2 | 4.2 |
| MG | 30.7 | 25.4 | 23.4 | 30.3 | 27.7 |
| DG | 44.2 | 50.9 | 49.7 | 45.7 | 48.1 |
| TG | 2.8 | 2.8 | 4.4 | 10.9 | 11.1 |
| MG/DG/TG | 77.7 | 79.2 | 77.4 | 87.0 | 86.8 |

Table VIII demonstrates that a consistently high degree of conversion (46–55%) was obtained in ten successive runs thereby establishing the productivity of the immobilised lipase. The recovery of EPA and DHA was consistently at least as good or better than that demonstrated in Table II for the lipase powder, even though only a fifth of the amount of lipase was used. Accordingly, the EPA plus DHA content in the glyceride product mixture remained very high indeed, ranging from 44–55%. The extent of the hydrolysis side reaction was slightly higher than in Table II, presumably as a result of the higher water content required for the immobilised lipase, although the water content of the reaction was still below the stipulated limit of 1%.

The results of the productivity experiments with PSL immobilised on Amberlite under exactly the same reaction conditions as for the Duolite case are given in Table IX.

TABLE IX

Productivity experiments with PSL on Amberlite.

| | | EPA | | | DHA | | |
|---|---|---|---|---|---|---|---|
| Run | % Conversion | Ar. % EE | Wt. % EE | Ar. % GL | Ar. % EE | Wt. % EE | Ar. % GL |
| 1 | 48.2 | 2.3 | 6.6 | 30.1 | 3.1 | 15.0 | 16.3 |
| 2 | 48.6 | 2.5 | 7.5 | 29.6 | 3.1 | 16.2 | 15.2 |
| 3 | 49.2 | 2.4 | 7.4 | 29.4 | 3.2 | 16.6 | 16.4 |
| 4 | 47.6 | 2.6 | 7.1 | 30.8 | 3.2 | 15.6 | 15.7 |
| 5 | 45.7 | 2.6 | 6.5 | 31.6 | 3.4 | 14.2 | 17.3 |
| 6 | 48.8 | 2.7 | 7.8 | 30.7 | 3.5 | 16.8 | 16.8 |
| 7 | 48.5 | 2.6 | 7.4 | 30.4 | 3.4 | 16.8 | 15.7 |
| 8 | 50.1 | 2.8 | 8.6 | 30.1 | 3.0 | 16.7 | 15.3 |

(Abbreviations: Ar. % = area %; GL = glyceride product = MG/DG/TG.).

It is clear from Table IX that the immobilisation on Amberlite was even more successful that the one on Duolite. The amount of immobilised lipase is only one-half that required on Duolite (one-tenth of the original amount of lipase powder) to obtain similar results. Thus, a consistent extent of conversion (48–50%) was obtained in eight successive runs after 24 hours reaction time with the EPA+DHA composition of the glyceride product mixture consistently remaining between 45 and 47%. The EPA and DHA recovery remained similar as did the extent of the hydrolysis side-reaction (water content below the stipulated limit of 1%, but results of hydrolysis not included in the table) as compared to the Duolite preparation.

EXAMPLE 5

The purpose of this experiment was to assess the activity of *Candida antarctica* lipase (CAL) and *Mucor miehei* lipase (MML) in the ethanolysis of a glyceride mixture produced by transesterifying a fish oil in the presence of PSL, as previously described.

(a) CAL ethanolysis of glycerides

Immobilised CAL (Novo-Nordisk, SP 435, 1–2% water-content; 0.5 g) was added to a glyceride mixture (2.5 g; approximately 8.5 mmol of ester equivalents; initial composition; 25.0% EPA and 15.1% DHA, produced by PSL-catalysed transesterification of a fish oil) and absolute ethanol (0.80 g, 17.4 mmol). The resulting enzyme suspension was gently stirred at room temperature under nitrogen. Samples were collected at appropriate times and analysed as previously described. The reaction was discontinued by separating off the enzyme by filtration after 22 hours.

The results are given in Table X below.

TABLE X

The progress of the ethanolysis of glyceride mixture with CAL at 20° C. (EE product).

| Time (min/hour) | 10 min | 20 min | 30 min | 40 min | 50 min |
|---|---|---|---|---|---|
| Wt. % EE | 12.7 | 20.3 | 29.1 | 29.0 | 35.8 |
| % A EPA | 29.0 | 29.3 | 30.2 | 34.5 | 29.4 |
| Wt. % EPA | 15.4 | 24.6 | 36.8 | 42.6 | 34.2 |
| % A DHA | 5.7 | 6.3 | 6.9 | 6.9 | 7.2 |
| Wt. % DHA | 5.4 | 9.5 | 14.7 | 14.7 | 14.7 |

| Time (min/hour) | 1 hour | 3 hours | 6 hours | 10 hours | 22 hours |
|---|---|---|---|---|---|
| Wt. % EE | 40.2 | 68.1 | 76.6 | 80.4 | 100.0 |
| % A EPA | 28.1 | 25.5 | 27.0 | 26.0 | 25.3 |
| Wt. % EPA | 47.1 | 72.6 | 83.4 | 83.9 | 98.0 |
| % A DHA | 7.1 | 8.2 | 10.3 | 10.4 | 14.8 |
| Wt. % DHA | 20.8 | 40.4 | 55.4 | 54.9 | 100.0 |

Table X demonstrates the progress of the ethanolysis of a glyceride mixture with CAL at 20° C. Approximately a two-fold excess of ethanol was used as based on mol equivalents of ester groups present in the initial glyceride mixture. Only the composition of the ethyl ester product is shown in the table. It can be seen that the reaction had proceeded to completion after 22 hours reaction time. Also, although the lipase displays high activity toward both EPA and DHA, it is evident that it displays considerably higher activity toward the former fatty acid, that, is EPA.

(b) MML ethanolysis of glycerides

The reaction conditions were identical to those of the CAL ethanolysis reaction described in (a) above. Immobilised MML (Novo-Nordisk, Lipozyme™, 10% water-content; 0.5 g) was added to the glyceride mixture (2.5 g; approximately 8.5 mmol of ester equivalents; initial composition: 25% EPA and 15.1% DHA, produced by PSL-catalysed transesterification of a fish oil) and absolute ethanol (0.80 g, 17.4 mmol). The resulting enzyme suspension was gently stirred at room temperature under nitrogen. Samples were collected at appropriate times and analysed as previously described. The reaction was discontinued by separating off the enzyme by filtration after 27 hours.

TABLE XI

The progress of the ethanolysis of glyceride mixture with MML at 20° C.

| Time | 1 h | 2 h | 3 h | 6 h | 9 h | 12 h | 27 h |
|---|---|---|---|---|---|---|---|
| % Conv. | 15.8 | 21.7 | 25.4 | 33.7 | 39.5 | 43.0 | 50.1 |
| Ethyl esters: | | | | | | | |
| % Area EPA | 25.4 | 28.7 | 30.4 | 32.1 | 31.5 | 32.3 | 28.4 |
| % (w/w) EPA | 14.4 | 24.1 | 27.5 | 39.3 | 47.1 | 50.2 | 55.0 |
| % Area DHA | 3.7 | 2.9 | 3.7 | 5.0 | 5.5 | 6.6 | 6.3 |
| % (w/w) DHA | 4.0 | 4.7 | 6.4 | 11.2 | 15.2 | 16.7 | 21.7 |
| Residual MG/DG/TG | | | | | | | |
| % area EPA | 26.4 | 26.5 | 30.1 | 23.1 | 21.8 | 20.8 | 20.9 |
| % (w/w) EPA | 85.6 | 75.9 | 72.5 | 60.7 | 52.9 | 49.8 | 45.0 |
| % area DHA | 18.3 | 20.9 | 23.2 | 23.2 | 23.0 | 22.9 | 24.9 |
| % (w/w) EPA | 96.0 | 95.7 | 93.6 | 88.8 | 86.8 | 83.3 | 78.3 |

It is evident from Table XI that MML displays a good degree of discrimination between EPA and DHA in the ethanolysis reaction of the EPA/DHA enriched glycerides. At 50% conversion, after 27 hours reaction time, about 80% of the initial DHA content remains in the residual glyceride mixture. The distribution of EPA was not quite as favourable, 55% in the ethyl esters and still 45% in the glyceride residue. This may be improved by running a second ethanolysis reaction on the glyceride residue under similar conditions. It should also be noted that the activity of MML provides a possibility of using EPA-enriched fish oil for producing EPA and DHA-enriched fish oil (e.q. tuna oil) for producing DHA by this methodology.

EXAMPLE 6

The purpose of this experiment was to demonstrate the applicability of the process of the invention to plant and vegetable oils.

PSL-catalysed Ethanolysis of Arachidonic Acid Extract (AA)

An arachidonic acid (AA, 20:4 n-6) extract, provided by Pronova Biocare, containing 31.1% AA was treated according to the method described in Example 1 for fish oil, that is, 10% PSL as powder, 20° C., 50% conversion, 24 hours.

The results are given in Table XII below.

TABLE XII

| Class | Wt. % class | Area % AA | Wt. % AA |
|---|---|---|---|
| EE | 50 | 7.6 | 12 |
| FFA | 2 | 23.3 | 1 |
| MG | 17 | 49.0 | 24 |
| DG | 24 | 57.4 | 47 |
| TG | 8 | 58.9 | 16 |
| MG/DG/TG | 49 | 54.2 | 87 |

Table XII demonstrates a very high recovery of AA in the glyceride mixture, 87% at 50% conversion, higher than DHA, but lower than EPA in the corresponding fish oil reactions. The extent of the hydrolysis side-reaction was comparable to that in the fish oil experiments, 2%. The AA content of the glyceride produce mixture was 54.2%. Surprisingly, it was highest in the TG fraction and lowest in the MG fraction.

We claim:

1. A process for treating an oil composition containing saturated, monounsaturated, and polyunsaturated fatty acids in the form of triglycerides, in order to obtain a refined product having a higher concentration of polyunsaturated fatty acids, which process comprises:

(a) subjecting the oil composition to a transesterification reaction with a $C_1$–$C_6$ alcohol under substantially anhydrous conditions and in the presence of a lipase to catalyze the transesterification of saturated and monounsaturated fatty acids more so than polyunsaturated fatty acids, the amount of water present in the reaction mixture being less than one weight percent and the amount of said $C_1$–$C_6$ alcohol present in the reaction mixture being not more than 15 molar equivalents based on the triglycerides present, so as to obtain a mixture of glyceride esters and alcohol esters;

(b) separating from said mixture a fraction containing esters of said $C_1$–$C_6$ alcohol with saturated and monounsaturated fatty acids produced by said lipase-catalyzed transesterification reaction; and (c) recovering as a residual glyceride fraction a refined oil product having a higher concentration of polyunsaturated fatty acids than said starting oil composition.

2. The process according to claim 1, wherein said lipase is in an immobilized form.

3. The process according to claim 1, wherein said $C_1$–$C_6$ alcohol is absolute ethanol.

4. The process according to claim 3, wherein the amount of said $C_1$–$C_6$ alcohol is from 2 to 5 molar equivalents based on the triglyceride present.

5. The process according to claim 1, wherein said transesterification reaction is carried out at room temperature.

6. The process according to claim 1, wherein said separation step (b) comprises one or more molecular distillations.

7. The process according to claim 1, wherein said oil composition is a marine oil composition or a fermentation product containing n-3 polyunsaturated fatty acids.

8. The process according to claim 1, wherein said lipase is one which is substantially inactive towards both eicosapentaenoic acid (EPA) and docosahexaenoic acid (DHA).

9. The process according to claim 8, wherein said lipase is *Pseudomonas cepacia* lipase or *Pseudomonas fluroescens* lipase.

10. A process according to claim 1, for the preparation of a composition containing at least 40% by weight of eicosapentaenoic acid (EPA) plus docosahexaenoic acid (DHA) comprising the further steps of:

(d) transesterifying the residual glyceride fraction with a lower alcohol in an alkaline environment using chemical catalysis, or by enzymatic catalysis using lipase;

(e) heating the resulting lower alkyl ester product with an excess of urea in an alkanol to a temperature of from 55° C. to 99° C.;

(f) cooling the product of step (e) to precipitate urea fatty acid alkyl ester adduct and thereafter separating off said adduct to leave a solution mainly containing n-3 fatty acid esters, the combined EPA plus DHA content of said solution being at least 40% of the total fatty acid content of the solution;

(g) separating from the solution remaining from step (f) a mixture of the n-3 fatty acid alkyl esters; (h) removing any solvent from the mixture obtained in step (g); and (h) recovering a concentrate containing at least 40% by weight of eicosapentaenoic acid (EPA) plus docosahexaenoic acid (DHA).

11. The process according to claim 10, wherein the concentrate obtained in step (h) is further concentrated by means of one or more steps of molecular distillation in order to increase the concentration of eicosapentaenoic acid (EPA) plus docosahexaenoic acid (DHA) therein to 85% or higher.

12. The process according to claim 1, for obtaining substantially pure eicosapentaenoic acid (EPA) and substantially pure docosahexaenoic acid (DHA) comprising the further steps of:

(d) transesterifying the residual glyceride fraction with a $C_1$–$C_6$ alcohol under substantially anhydrous conditions and in the presence of a lipase active to preferentially catalyze the esterification of EPA;

(e) separating the resulting EPA-enriched $C_1$–$C_6$ alcohol ester fraction and the residual DHA-enriched glyceride mixture;

(f) working up the EPA-$C_1$–$C_6$ alcohol ester fraction and concentrating the EPA fraction;

(g) transesterifying the DHA-enriched glyceride mixture with a $C_1$–$C_6$ alcohol in the presence of a lipase active to catalyze the esterification of DHA;

(h) working up the resulting DHA-$C_1$–$C_6$ alcohol ester fraction and concentrating the DHA fraction; and (i) recovering both a substantially 100% pure EPA and a substantially 100% pure DHA.

13. The process according to claim 12 wherein the lipase used in step (d) is *Mucor miehei* lipase.

14. The process according to claim 12 or claim 13 wherein the lipase used in step (g) is *Candida antarctica* lipase.

15. The process according to claim 12 wherein the $C_1$–$C_6$ alcohol in steps (d) and/or (g) is ethanol.

16. The process according to claim 1 wherein said oil composition is a plant or vegetable oil composition or a fermentation product containing n-6 polyunsaturated fatty acids.

17. The process according to claim 16, wherein said lipase is one which is substantially inactive towards arachidonic acid (AA).

18. The process according to claim 17, wherein said lipase is *Pseudomonas cepacia* lipase or *Pseudomonas fluroescens* lipase.

19. The process according to claim 1, for the preparation of a composition containing at least 40% by weight of arachidonic acids comprising the further steps of:

(d) transesterifying the residual glyceride fraction with a lower alcohol in an alkaline environment using chemical catalysis, or by enzymatic catalysis using lipase;

(e) heating the resulting alkyl ester product with an excess of urea in an alkanol to a temperature of from 55° C. to 99° C.;

(f) cooling the product of step (d) to precipitate urea fatty acid alkyl ester adduct and thereafter separating off said adduct to leave a solution mainly containing n-6 fatty acid esters, the arachidonic acid content of said solution being at least 40% by weight of the total fatty acid content of the solution;

(g) separating from the solution remaining from step (e) a mixture of the n-6 fatty acid alkyl esters;

(h) removing any solvent from the mixture obtained in step (g); and (i) recovering a composition containing at least 40% by weight of arachidonic acid.

20. The process according to claim 19, wherein the composition recovered in step (i) is further concentrated by means of one or more steps of molecular distillation in order to increase the concentration of arachidonic acid therein to 85% or higher.

21. The process according to claim 20 wherein the arachidonic acid fraction is concentrated to substantially 100% purity.

22. A process for the removal of environmental pollutants from an oil composition containing one or more such pollutants in admixture with saturated, monounsaturated, and polyunsaturated fatty acids in the form of triglycerides, which process comprises the steps of:
  (a) subjecting the oil composition to a transesterification reaction with a $C_1$–$C_6$ alcohol under substantially anhydrous conditions and in the presence of a lipase to catalyze the transesterification of saturated and monounsaturated fatty acids more so than polyunsaturated fatty acids, the amount of water present in the reaction mixture being less than one weight percent and the amount of said $C_1$–$C_6$ alcohol present in the reaction mixture being not more than 15 molar equivalents based on the triglycerides present, so as to obtain a mixture of glyceride esters and alcohol esters;
  (b) subjecting the mixture obtained in step (a) to one or more molecular distillations to distill off an alcohol ester fraction containing some amount of said environmental pollutant or pollutants; and
  (c) recovering as a residual glyceride fraction an oil product having a lower concentration of environmental pollutants than said starting oil composition.

23. The process according to claim 22, wherein said step (a) is conducted with a lipase in an immobilized form.

24. The process according to claim 22, wherein said step (a) is conducted using absolute ethanol as the $C_1$–$C_6$ alcohol.

25. The process according to claim 22, wherein, in said step (a), the amount of said $C_1$–$C_6$ alcohol used is from 2 to 5 molar equivalents, based on the triglyceride present.

26. The process according to claim 22, wherein said step (a) is carried out at room temperature.

27. The process according to claims 1, 10, 12, 19 or 22, wherein the total amount of water present in the reaction mixture in step (a) is less than 0.5%, weight/weight.

28. The process according to claims 1, 10, 12, 19 or 22, wherein the total amount of water present in the reaction mixture in step (a) is between 0.1 and 0.25%, weight/weight.

29. The process according to claims 1, 10, 12, 19 or 22, wherein the reaction mixture in step (a) is in the absence of solvent.

* * * * *

UNITED STATES PATENT AND TRADEMARK OFFICE
CERTIFICATE OF CORRECTION

PATENT NO. : 5,945,318  
DATED : August 31, 1999  
INVENTOR(S) : Harald Breivik et al.

Page 1 of 3

It is certified that error appears in the above-identified patent and that said Letters Patent is hereby corrected as shown below:

Title page,
Item [56], References Cited,
FOREIGN PATENT DOCUMENTS, "WO90/13656 11/1990 WIPO." (second occurrence) should be deleted; and
"WO91/16443 10/1991 WIPO." (second occurrence) should be deleted.

Column 2,
Line 4, "DRA" should read -- DHA --.

Column 3,
Line 4, "*cylinracea*" should read -- *cylindracea* --;
Line 11, "is" should be deleted; and
Line 15, "*cylinracea*" should read -- *cylindracea* --.

Column 5,
Line 27, "*cylinracea*" should read -- *cylindracea* --; and
Line 28, "*roguefortii*" should read -- *roquefortii* --.

Column 7,
Line 21, "mixture i.e." should read -- mixture, i.e., --.

Column 8,
Line 12, "mild e.g." should read -- mild, e.g., --.

Column 9,
Line 16, "more e.g." should read -- more, e.g., --;
Line 22, "ester" should read -- ethyl ester --;
Line 32, "fraction e.g." should read -- fraction, e.g., --;
Line 34, "enzymatically e.g." should read -- enzymatically, e.g., --; and
Line 51, "favours" should read -- favors --.

Column 10,
Line 11, "fraction e.g." should read -- fraction, e.g., --;
Line 30, "sources e.g." should read -- sources, e.g., --; and
Line 46, "*fluroescens*" should read -- *fluorescens* --.

Column 11,
Line 9, inside the table, first column, "rogueforti" should read -- roquefortii --; and
Line 49, "$C_{21:01}$" should read -- $C_{21:0}$, --.

UNITED STATES PATENT AND TRADEMARK OFFICE
CERTIFICATE OF CORRECTION

PATENT NO. : 5,945,318
DATED : August 31, 1999
INVENTOR(S) : Harald Breivik et al.

It is certified that error appears in the above-identified patent and that said Letters Patent is hereby corrected as shown below:

Column 13,
Line 1 of the text below Table I - continued and the footnote, "*cylinracea*" should read -- *cylindracea* --.

Column 15,
Line 39, "Area a" should read -- Area % --;
Line 46, "favour" should read -- favor --; and
Line 47, "behaviour" should read -- behavior --.

Column 18,
Line 38, "Prepa-" should read -- prepa --; and
Line 55, "(log)" should read -- (10 g) --.

Column 22,
Line 2, "27 hours." should read -- 27 hours.

The progress of the ethanolysis of the same glyceride sample as used in the CAL reaction with MML at 20° C. is demonstrated in Table XI, below. --;
Line 19, inside Table XI, first column "EPA" should read -- DHA --;
Line 28, "favourable" should read -- favorable --; and
Line 33, "e.q." should read -- e.g., --.

Column 23, claim 9,
Line 2, "*fluroescens*" should read -- *fluorescens* --;

Column 23, claim 10,
Line 18, "esters; (h) removing" should read -- esters; (h) removing --; and
Line 20, "(h)" should read -- (i) --.

Column 23, claim 11,
Line 2, "(h)" should read -- (i) --.

Column 24, claim 18,
Line 2, "*fluroescens*" should read -- *fluorescens* --.

Column 24, claim 19,
Line 3, "acids" should read -- acid, --;
Line 10, "(d)" should read -- (e) --; and
Line 16, "(e)" should read -- (f) --.

UNITED STATES PATENT AND TRADEMARK OFFICE
CERTIFICATE OF CORRECTION

PATENT NO. : 5,945,318
DATED : August 31, 1999
INVENTOR(S) : Harald Breivik et al.

It is certified that error appears in the above-identified patent and that said Letters Patent is hereby corrected as shown below:

Column 26, claim 29,
Line 3, "solvent" should read -- a solvent --.

Signed and Sealed this

Eighteenth Day of December, 2001

Attest:

Attesting Officer

JAMES E. ROGAN
Director of the United States Patent and Trademark Office